United States Patent
Butler (10) Patent No.: US 9,820,644 B2
(45) Date of Patent: *Nov. 21, 2017

(54) GLARE ASSEMBLY FOR EYE TEST DISPLAY

(71) Applicant: M&S TECHNOLOGIES, INC., Niles, IL (US)

(72) Inventor: Kevin A. Butler, Niles, IL (US)

(73) Assignee: M&S TECHNOLOGIES, INC., Niles, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,239

(22) Filed: Aug. 15, 2016

(65) Prior Publication Data

US 2017/0127935 A1    May 11, 2017

Related U.S. Application Data

(63) Continuation of application No. 14/673,149, filed on Mar. 10, 2015, now Pat. No. 9,433,347, which is a continuation-in-part of application No. 14/047,467, filed on Oct. 7, 2013, now Pat. No. 8,992,022, which is a continuation of application No. 12/911,473, filed on Oct. 25, 2010, now Pat. No. 8,550,631.

(60) Provisional application No. 61/254,410, filed on Oct. 23, 2009.

(51) Int. Cl.
| | |
|---|---|
| *A61B 3/02* | (2006.01) |
| *A61B 3/00* | (2006.01) |
| *A61B 3/10* | (2006.01) |
| *A61B 3/06* | (2006.01) |
| *A61B 3/032* | (2006.01) |

(52) U.S. Cl.
CPC .............. *A61B 3/063* (2013.01); *A61B 3/005* (2013.01); *A61B 3/0008* (2013.01); *A61B 3/032* (2013.01)

(58) Field of Classification Search
CPC ....... A61B 3/032; A61B 3/024; A61B 3/1015; A61B 3/103; A61B 3/1225; A61H 5/00
USPC ....... 351/243, 239, 222, 246, 200, 203, 205, 351/221, 223, 224
See application file for complete search history.

(56) References Cited

U.S. PATENT DOCUMENTS

| | | | |
|---|---|---|---|
| 4,800,404 | A | 1/1989 | Ginsburg et al. |
| 5,365,370 | A | 11/1994 | Hudgins |
| 5,969,792 | A | 10/1999 | Ginsburg |
| 6,783,239 | B2 | 8/2004 | Epitropoulos |
| 7,204,591 | B2 | 4/2007 | Wertheim et al. |

*Primary Examiner* — Dawayne A Pinkney
(74) *Attorney, Agent, or Firm* — Fay Sharpe LLP (57) ABSTRACT

A monitor/display is used to display a vision test. A patient is spaced a predetermined distance from the monitor/display during the testing procedure, and individual, multiple LED housings are equally spaced about a center point of the monitor/display to direct light toward the patient during at least a portion of the test procedure. The light emanating from the individual housings is a diffuse, unfocused light to simulate glare, and the intensity of the light may be selectively altered. Conducting vision testing under glare conditions determines if there is any reduction or fall off in the patient's vision under such circumstances and provides an Indication of whether the patient may require cataract surgery or has another ocular problem. An assembly allows an existing vision testing system to be easily modified to provide glare light testing capabilities.

20 Claims, 6 Drawing Sheets

GLARE ASSEMBLY FOR EYE TEST DISPLAY

This continuation application claims the priority benefit of continuation-in-part application Ser. No. 14/673,149, filed 30 Mar. 2015, which claims the priority benefit of U.S. application Ser. No. 14/047,467, filed Oct. 7, 2013, now U.S. Pat. No. 8,992,022, which is a continuation of and claims the priority benefit of Ser. No. 12/911,473, filed 25 Oct. 2010, now U.S. Pat. No. 8,550,631, which application claims the priority benefit of U.S. provisional application Ser. No. 61/254,410, filed 23 Oct. 2009, the disclosure of each case is expressly incorporated herein in its entirety.

BACKGROUND OF THE DISCLOSURE

This disclosure relates to an eye test assembly, and more particularly to an eye test assembly that displays an eye chart on a computer monitor and the eye test is run by software or a conventional vision test shown a projector display. Further, the present disclosure relates to a glare assembly for use with such a display or monitor that s useful in diagnosing cataracts or other ocular problems or issues associated with a patient. Under normal testing conditions, a patient may demonstrate acceptable scores, for example even exhibiting 20/20 vision in an examination room under normal exam room conditions. Unfortunately, in the light of day, and in real world conditions, such as driving at night with oncoming headlights directed at the driver, or in bright sunlight, the patient's vision may be quite different due to bright light passing through the lens of the eye.

There are a couple of different products presently on the market that test for the impact of glare, for example, a Brightness Acuity Tester (BAT), as shown and described in U.S. Pat. No. 4,784,483. The disclosure of that patent is hereby incorporated by reference. An upright handle positions an open sided housing having an aperture or opening through the housing adjacent a patient's eye. A source of illumination is disposed in the housing and is varied between high, medium, and low settings. In this manner, a patient's vision is measured in a standard manner, and with one eye occluded, the brightness acuity tester is held adjacent the patient's eye under examination, the source of illumination turned on, and visual acuity of that eye is then measured with the patient looking through the glare light. In other words, glare light is purposefully introduced into the visual path of the patient. The comparison between these acuity testing procedures under non-glare and glare conditions will then determine whether the patient has any pronounced or recognizable change in acuity vision. This may be an indication of whether cataracts or other ocular problems exist.

Another type of commercially available device is one sold by Vector Vision. An illuminated eye chart box, or light box, for example the type as shown and described in U.S. Pat. No. 5,078,486, is modified to include first and second halogen lights secured on either side of the light box. The halogen lights are described as simulating an on-coming car with headlamps illuminated at a preselected distance. The halogen lights are either turned on or off. A particular line or row of characters on the light box is illuminated. An internal light source generates the desired light intensity on a particular row of the eye chart, and employs a sensor or photocell to monitor the light intensity in the ambient environment adjacent the eye chart. In this manner, the amount of light generated by the light source can be altered.

Although commercially successful, improvements are desired, particularly when used with a vision testing arrangement.

SUMMARY

A computer vision testing system includes a monitor/display for displaying a test procedure. Individual, multiple light sources are equi-spaced about a center point of the monitor/display and directed toward an associated patient to conduct the test procedure under glare light conditions.

A method of conducting vision testing on a patient includes locating a monitor/display a predetermined distance from an associated patient, running a vision test, displaying the test on the monitor/display, and directing light from individual light sources equi-spaced from a center point of the monitor/display toward the associated patient.

An assembly or kit is provided for modifying an existing vision testing system wherein the system includes a monitor/display for displaying a vision test procedure to include glare test capability. The assembly includes first, second, third, and fourth glare light sources. First, second, third, and fourth light brackets each include a cavity dimensioned to receive a respective one of the glare light sources therein and mount respective glare light sources at equi-spaced locations about a center point of the monitor/display and directed the glare light sources toward an associated patient to conduct the vision test procedure under glare light conditions.

A method of converting an existing vision testing system wherein the system includes a monitor/display for displaying a test procedure to include glare light test capability includes providing first, second, third and fourth glare light sources. The method further includes mounting the first, second, third and fourth glare light sources with first, second, third, and fourth light brackets at equi-spaced locations about a center point of the monitor/display.

A primary benefit is the ability to easily convert existing vision testing equipment to add glare light testing capabilities.

Another advantage is the ability to modify existing vision testing equipment without adversely impacting the original installation.

Still other benefits and advantages will become apparent to those skilled in the art upon reading and understanding the following detailed description.

DETAILED DESCRIPTION OF THE PREFERRED EMBODIMENTS

Figure 1:
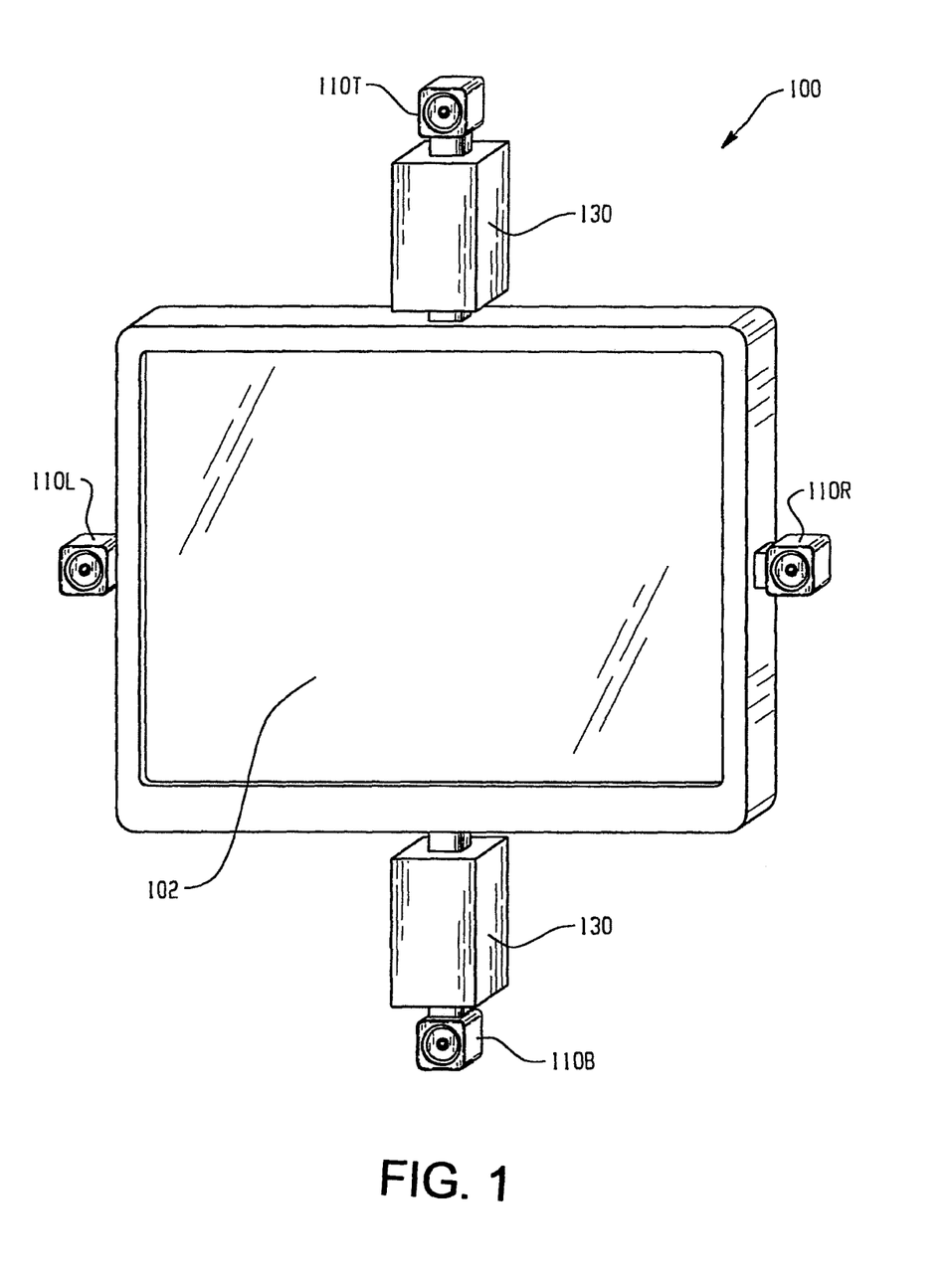
FIG. 1 is an elevational view of a computer monitor used as a display for conducting visual acuity testing.

Turning first to FIG. 1, there is a shown a monitor 100 used to display a vision test operated by software from an associated computer (not shown), for example, of the type as shown and described in U.S. Published Application No. 20040036840A1. The illustrated monitor is rectangular, for example having a 16×9 rectangular aspect ratio. Although the illustrated monitor is of a liquid crystal display (LCD) type, it is also contemplated that other types of monitor such as a cathode ray tube (CRT), LED, etc. monitor could be employed without departing from the scope and intent of the present disclosure. Display face 102 is controlled by the vision testing software. The testing usually occurs in a dark room in order to provide greater control over the luminance associated with the monitor and thus a more standardized testing. A patient is spaced a predetermined distance from the monitor during the testing procedure, and the size of the characters on the screen are controlled and calibrated.

Figure 2:
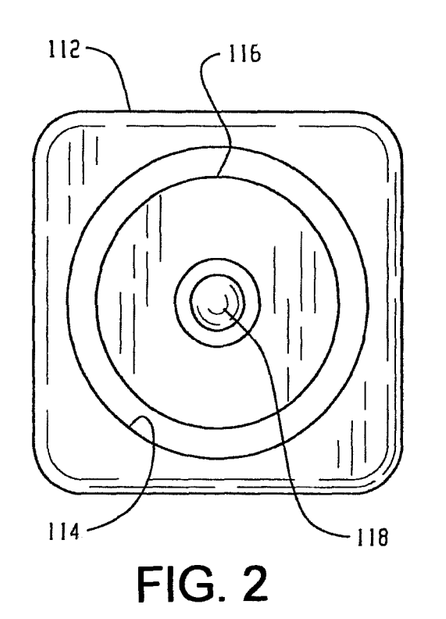
FIG. 2 is a plan view of one of the LED light sources.
Figure 3:
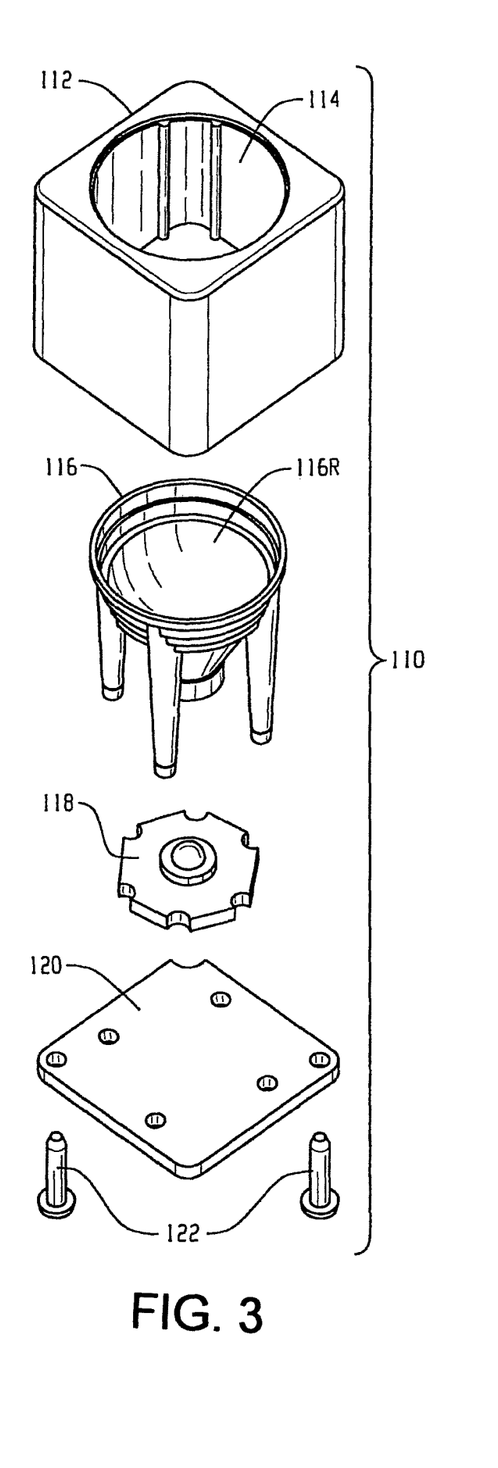
FIG. 3 is an exploded perspective view of one of the LED assemblies.

Preferably, multiple LEDs 110 of a glare light testing assembly are displayed around the monitor. Each LED 110 is of substantially identical structure as shown in FIGS. 2 and 3. For example, housing 112 includes an opening 114 along one surface of the generally cubical-shaped housing, although other housing conformations may be adopted without departing from the scope and intent of the present disclosure. The hollow housing receives a frame lens and holder 116 that serves to direct light emitted from the LED through an opening 114 in the housing. For example, an inner reflective surface 116R reflects and directs light outward through the housing opening and toward the patient (not shown) who is typically seated a predetermined distance from the monitor. An LED light source 118 is mounted at one end of the holder 116 in order to direct light therethrough and ultimately through the opening 114 of the housing. A heat sink 120 is advantageously located on a rear surface of the light source in order to convey heat away from the elevated temperatures associated with operation of the LED. One or more fasteners, such as threaded screws 122 extend through the heat sink and into the LED housing in order to contain the light source in operative engagement with the lens and holder within the LED housing.

Each housing assembly 110 of the glare light testing assembly is then mounted to the perimeter of the monitor 100. Each LED housing disposed on a side portion of the monitor, i.e., on the right-hand and left-hand sides of the monitor are preferably disposed closely adjacent the perimeter of the monitor. As will be appreciated, in this manner, and with the display face centered within the perimeter of the monitor, the housing assemblies 110 are equi-spaced from a left-to-right center portion of the display face, and preferably at equal distances from the center. For ease of reference, these housing assemblies are referred to as 110L and 110R. Further, additional LED housing assemblies 110T, 110B are provided on extensions 130 that space the top and bottom LED housing assemblies from the upper and lower perimeters, respectively, of the monitor. Each of the housing assemblies is centered left-to-right, and preferably equi-spaced top-to-bottom away from a central point in a monitor, i.e., by the same distance as each of the LED housing assemblies 110L, 110R. In this manner, each LED housing is equally spaced from the center point of the monitor 100.

Using at least four perimeter spaced light sources is also preferred to simulate a circle of light. In some instances, a pair of light sources (either positioned on either side or spaced top to bottom) may be insufficient. Further, the light emanating from the individual housings is a diffuse light, i.e., not focused light. Ultimately, a diffuse light source that is provided in a relatively even manner from the periphery of the screen to simulate glare is desirable for glare testing.

Conducting vision testing under glare conditions to determine if there is any reduction or fall off in the patient's vision under such circumstances provides an indication, for example, of whether the patient may require cataract surgery or has another ocular problem.

Each LED housing assembly connects to the computer assembly, preferably through a USB port or the like, and in the presently preferred arrangement communicates with the processor through a serial-type protocol. Of course, other communication arrangements or connections may be used without departing from the scope and intent of the present disclosure. The processor controls not only an on/off condition of the LEDs, but also allows the brightness of each to be adjusted between one of approximately two-hundred ten (210) levels of brightness. The intensity of the three watt LEDs supplied by a twenty four (24) volt power supply will vary depending on the distance from the patient. Since the distance of the patient from the monitor can be inputted to the software, the software can then compute a desired intensity level of brightness based on this measurement distance. Thus, although there are generally three general levels (high, medium and low which are dependent on the measurement distance of the patient from the light source), the levels of glare light intensity can be further manipulated with the teachings of the present disclosure if so desired. The patient can be tested in a variety of ambient light conditions because the glare lights can be adjusted.

Preferably, each of the LED housing assemblies that serve to provide glare light provides a diffuse light source that faces the patient. Particularly, with two, and preferably four or more LED housing assemblies, a more uniform diffused glare light is directed toward the patient while the vision testing is undertaken under the glare light condition.

Figure 4:
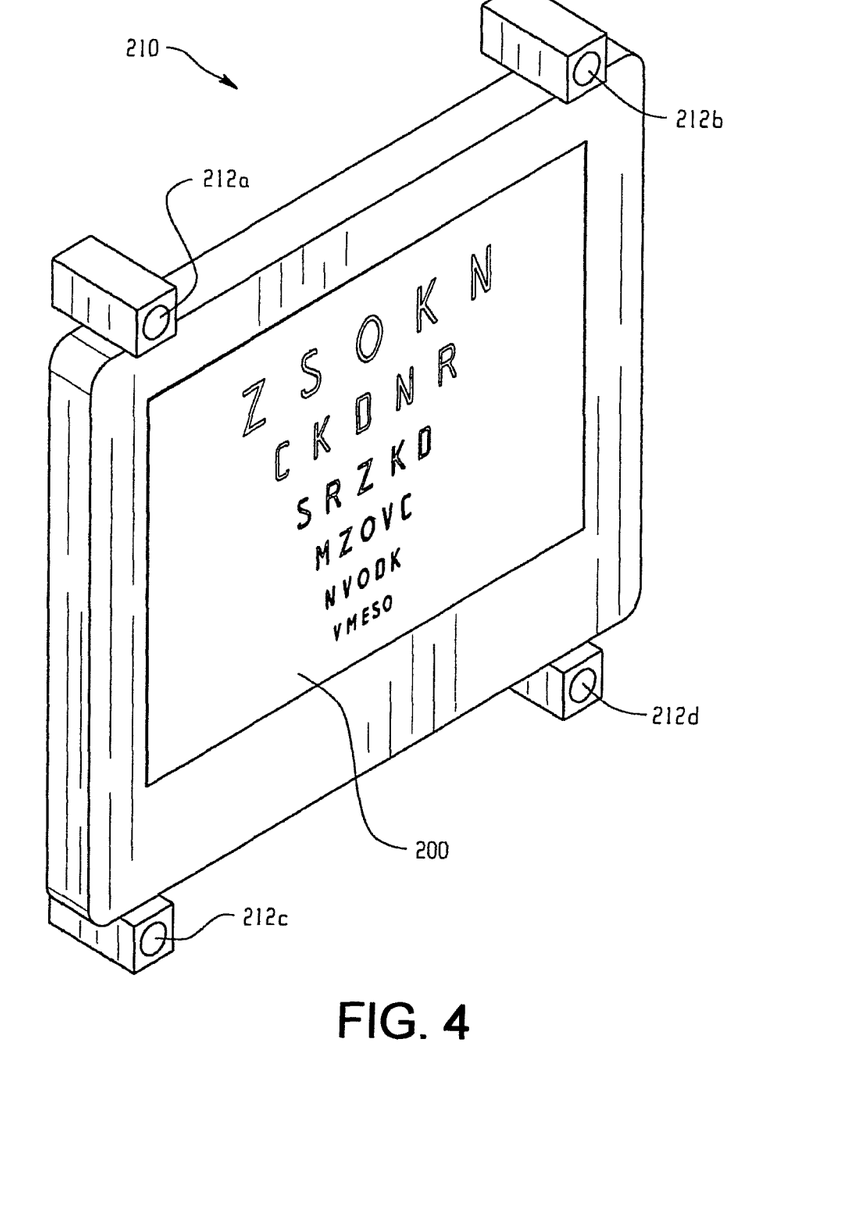
FIG. 4 of a monitor used as a display for conducting visual and that incorporates four glare light sources.
Figure 5:
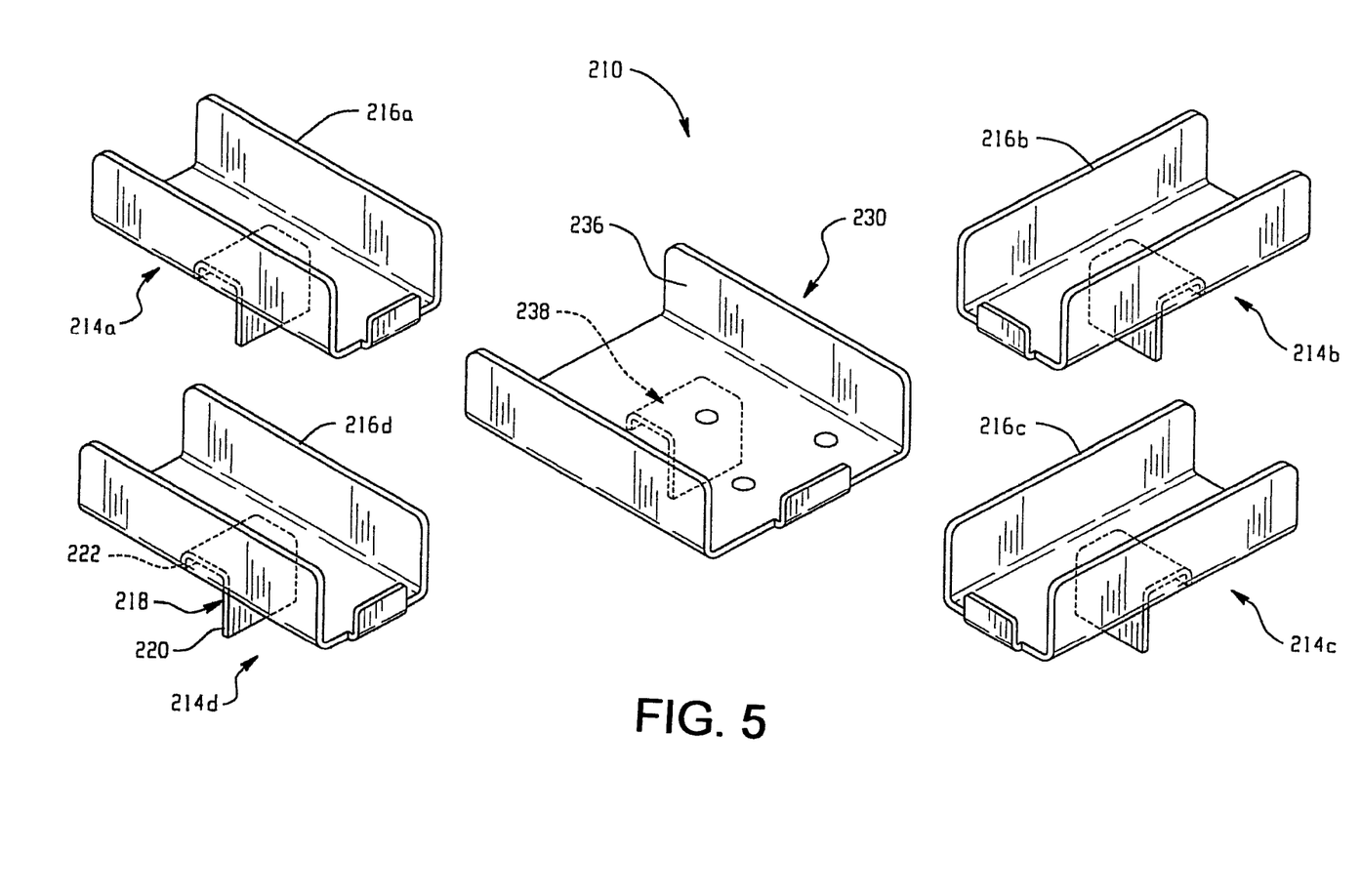
FIG. 5 shows an assembly that includes five brackets for mounting glare light sources and an infrared detector (not shown).
Figure 6:
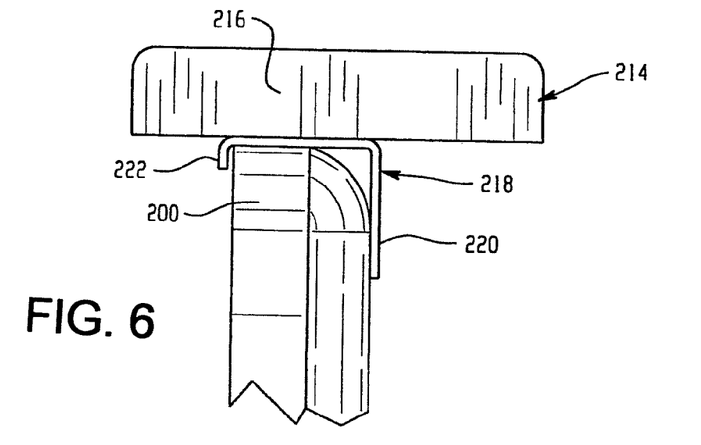
FIG. 6 shows one of the glare light source mounting brackets mounted on a perimeter of the monitor.

In FIGS. 4-6, an elongated, generally rectangular monitor or projector display 200 of a vision testing system is shown. The above-described LED glare light sources (referred to herein as glare light sources 202) of FIG. 3 can be similarly used in the vision testing system with the elongated, rectangular display/monitor 200 of FIGS. 4-6. An assembly or kit 210 includes a first light source 212a and a second light source 212b that are both mounted on an upper surface or edge of the display/monitor 200. Likewise, the assembly 210 includes a third glare light source 212c and fourth glare light source 212d that are mounted on a lower surface or edge of the display/monitor 200. As is evident in FIG. 5, four identical brackets 214a-d are shown for mounting the glare light sources 212a-d. In this preferred arrangement, each of the brackets 214a-d is identical and in a simplified form each bracket includes a first, channel-shaped portion 216 (that has a generally U-shape) that is dimensioned to receive or at least partially encompass an outer perimeter of the body of one of the LED glare light sources 212a-d to securely hold the glare light source in a desired position, and a second, channel-shaped portion 218 (that in this specific arrangement has a generally L-shape where one leg 220 is longer than the other leg 222) that is dimensioned for receipt over the perimeter of the display/monitor 200 and that secures the glare light source to the vision testing system. The shorter leg 222 is preferably located to extend over the front face of the display/monitor 200 so that the shorter leg does not interfere with the display region of the display/monitor (FIG. 6).

The fifth bracket 230 is not shown mounted on the monitor 200 of FIG. 4, however, it is understood that the fifth bracket receives a controller/converter or detector (such as an infrared detector) that cooperates with a remote control (not shown in this figure) to control the operation of the glare light sources, e.g., on/off, intensity, flashing, etc. In a manner similar to the other brackets 214a-d, the fifth bracket 230 likewise includes a first, channel-shaped portion 236 that is dimensioned to receive the detector (e.g., portion 236 at least partially encompasses an outer perimeter of the detector), and a second, channel-shaped portion 238 that is dimensioned for receipt over a perimeter portion of the monitor 200 to secure the glare light source to the vision testing system. Again, a shorter leg of the channel-shaped portion 238 is preferably received over the front face of the display/monitor 200 so as not to interfere with the display region of the display/monitor.

Figure 7:
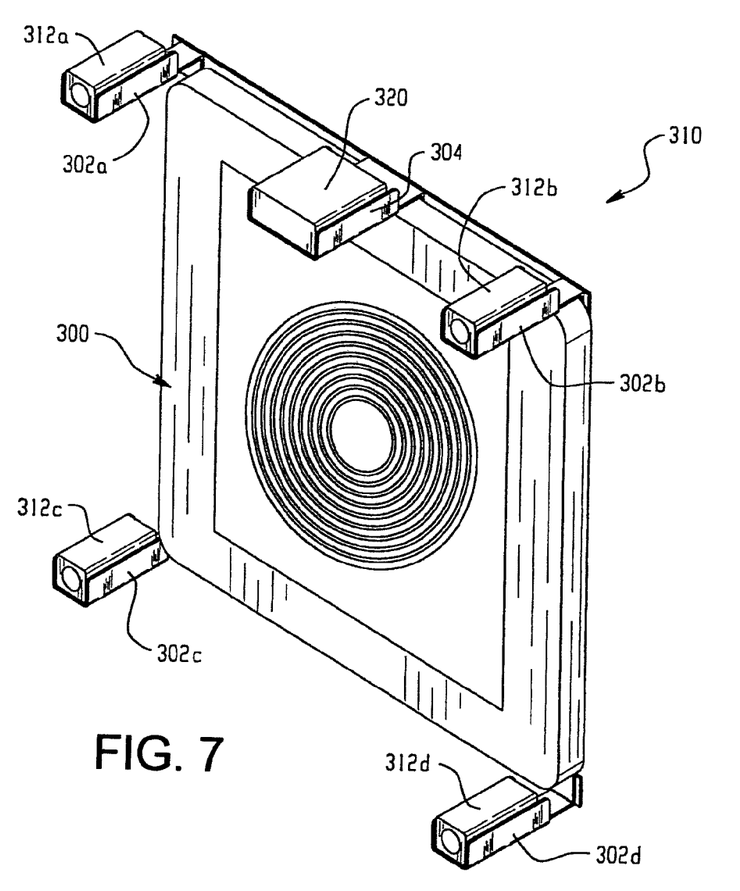
FIG. 7 shows a mirror display with glare light sources and a detector surrounding the display.
Figure 8:
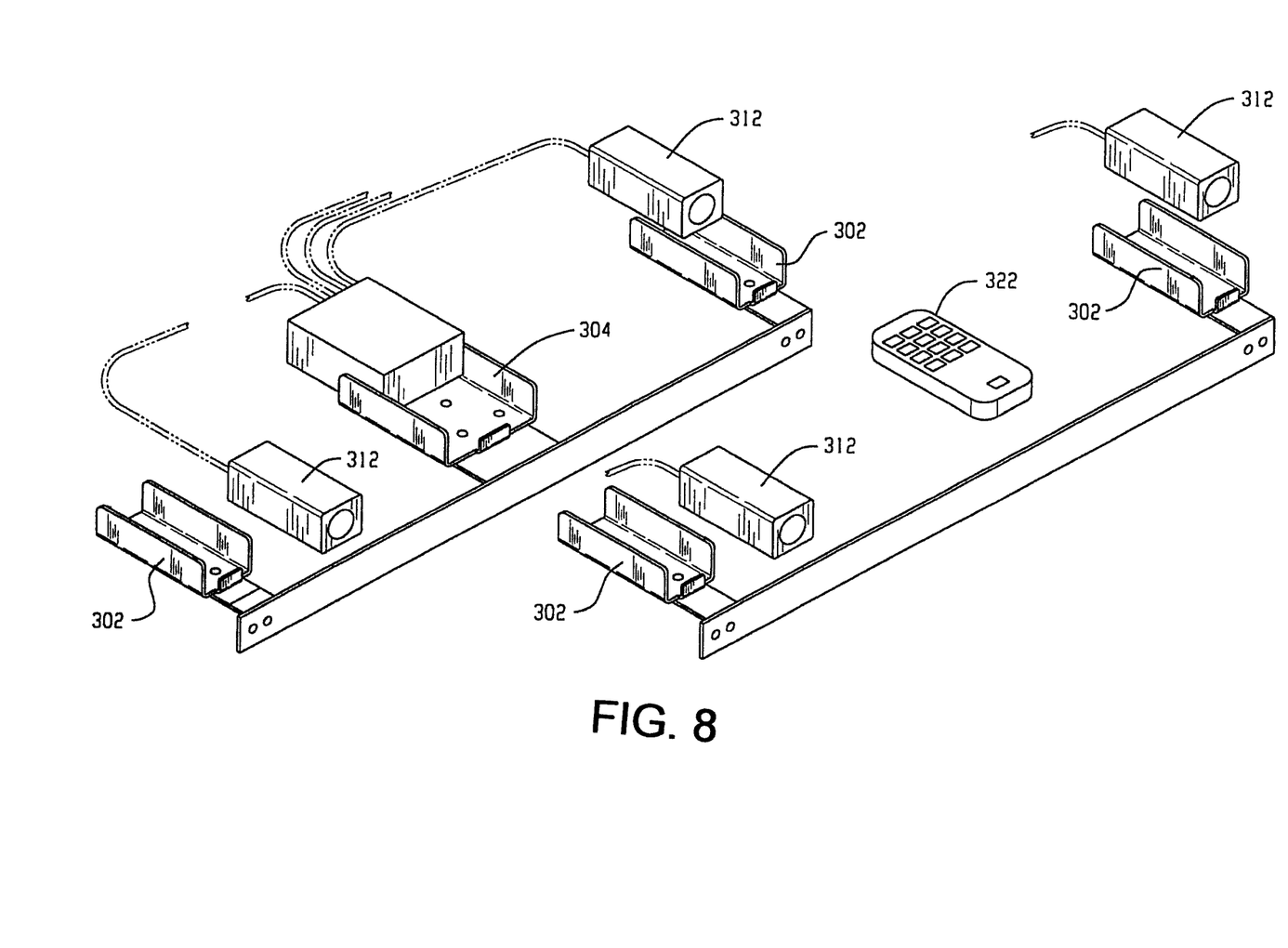
FIG. 8 separately shows the wall mounting assembly for the embodiment of FIG. 7.

The embodiment of FIGS. 7-8 is similar. An existing monitor or mirror display 300 can be converted with assembly or kit 310 to provide for glare light capabilities during vision testing. The assembly 310 includes four brackets 302 that are dimensioned to receive at least a portion of the body of a respective individual glare light source 312 therein. In this arrangement, each of the four brackets 302 is mounted to a support member, more particularly two brackets 302a, 302b are mounted to a first support member 320, and two brackets 302c, 302d are mounted to a second support member 322. The fifth bracket 304 is also mounted to the first support member 320 and dimensioned to receive the converter/detector 320 that cooperates with a remote controller 322. The detector 320 receives signals from a remote controller 322 to control the operation of the glare light sources 312, e.g., on/off, level of brightness, blinking, flashing, etc. Preferably, all four glare light sources 312 are connected to the detector via ports on the detector that receive cable connections. In this manner, the glare light sources 312 advantageously receive power through the detector, and signals from the detector 320 that allow the vision test system operator or protocol to control the glare light emitted from the glare light sources. Moreover, installation of the glare light assembly to work with the vision testing system can be accomplished without physically joining the components to the existing display/monitor 300 (here in FIG. 6, the support members that include the glare light sources and detector mounted thereto via brackets are secured to the wall adjacent the mirror display, and the mirror display is not secured to the support members and can be adjusted relative to the mounted glare light assembly) or alternatively the support members can be used to integrally join the individual glare light sources and the controller (detector) for the light sources to the vision testing system (e.g., to the monitor/display). Any one of the above-described assemblies of FIGS. 4-8 permits an existing vision testing system to be easily converted to accommodate glare light testing capabilities.

This written description uses examples to describe the disclosure, including the best mode, and also to enable any person skilled in the art to make and use the disclosure. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. Moreover, this disclosure is intended to seek protection for a combination of components and/or steps and a combination of claims as originally presented for examination, as well as seek potential protection for other combinations of components and/or steps and combinations of claims during prosecution.

What is claimed is:

1. An assembly for modifying an existing vision testing system wherein the system includes a monitor/display for displaying a test procedure to include glare test capability, the assembly comprising:
    at least first and second glare light sources;
    at least first and second light brackets each including a cavity dimensioned to receive a respective one of the glare light sources therein at equally-spaced locations relative to a center point of the monitor/display and directed toward an associated patient to conduct the test procedure under glare light conditions; and
    a detector in operative communication with the at least first and second glare light sources to provide signals thereto that control glare light emitted from the glare light sources in a uniform, diffuse and unfocused manner, that simulates a circle of light.

2. The assembly of claim 1 further comprising a support member to which the first and second glare light sources are mounted.

3. The assembly of claim 2 wherein the detector is mounted to the support member.

4. The assembly of claim 2 further comprising first and second brackets secured to the mounting member that receive the first and second glare light sources, respectively.

5. The assembly of claim 4 wherein the first and second brackets are secured to the mounting member in spaced relation.

6. The assembly of claim 5 wherein the first and second brackets are located outside a width dimension of the associated monitor/display of the vision testing system.

7. The assembly of claim 2 further comprising a third bracket secured to the mounting member, the third bracket configured to receive the detector.

8. The assembly of claim 2 wherein the support member is mounted to an associated wall surface.

9. The assembly of claim 2 wherein the support member is secured to a wall surface independently of the associated monitor/display of the vision testing system.

10. The assembly of claim 2 wherein the support member joins the glare light sources and detector to the vision testing system.

11. A method of modifying an existing vision testing system wherein the system includes a monitor/display for displaying a test procedure to include glare test capability, the comprising comprising:
    providing at least first and second glare light sources;
    providing at least first and second light brackets each including a cavity dimensioned to receive a respective one of the glare light sources therein at equally-spaced locations relative to a center point of the monitor/display and directed toward an associated patient to conduct the test procedure under glare light conditions;
    providing a detector that operatively communicates with the first and second glare light sources to provide signals thereto that control glare light emitted from the glare light sources; and
    operating the detector to provide uniform, diffuse and unfocused glare light that simulates a circle of light from the at least first and second glare light sources.

12. The method of claim 11 further comprising a support member to which the first and second glare light sources are mounted.

13. The method of claim 12 wherein the detector is mounted to the support member.

14. The method of claim 12 further comprising first and second brackets secured to the mounting member that receive the first and second glare light sources, respectively.

15. The method of claim 14 wherein the first and second brackets are secured to the mounting member in spaced relation.

16. The method of claim 15 wherein the first and second brackets are located outside a width dimension of the associated monitor/display of the vision testing system.

17. The method of claim 12 further comprising a third bracket secured to the mounting member, the third bracket configured to receive the detector.

18. The method of claim 12 wherein the support member is mounted to an associated wall surface.

19. The method of claim 12 wherein the support member is secured to a wall surface independently of the associated monitor/display of the vision testing system.

20. The method of claim 12 wherein the support member joins the glare light sources and detector to the vision testing system.

* * * * *